US009968145B2

(12) United States Patent
Hull (10) Patent No.: US 9,968,145 B2
(45) Date of Patent: May 15, 2018

(54) PATTERNED MEDICAL GLOVE FOR USE WHEN TAKING A PULSE

(71) Applicant: Summit Glove Inc., Minerva, OH (US)

(72) Inventor: James L. Hull, Malvern, OH (US)

(73) Assignee: Summit Glove Inc., Minerva, OH (US)

( * ) Notice: Subject to any disclaimer, the term of this patent is extended or adjusted under 35 U.S.C. 154(b) by 0 days. days.

(21) Appl. No.: 15/289,226

(22) Filed: Oct. 10, 2016

(65) Prior Publication Data

US 2017/0020213 A1    Jan. 26, 2017

Related U.S. Application Data

(63) Continuation of application No. 15/136,191, filed on Apr. 22, 2016.

(60) Provisional application No. 62/152,302, filed on Apr. 24, 2015.

(51) Int. Cl.
*A41D 19/00* (2006.01)

(52) U.S. Cl.
CPC ......... *A41D 19/0082* (2013.01); *A41D 19/00* (2013.01); *A41D 19/001* (2013.01); *A41D 19/0003* (2013.01); *A41D 19/0058* (2013.01); *A41D 2600/20* (2013.01)

(58) Field of Classification Search
CPC .. A61B 19/04; A41D 19/00; A41D 19/01547; A63B 71/146
USPC .............. 2/161.7, 159, 161.3, 161.8, 163
See application file for complete search history.

(56) References Cited

U.S. PATENT DOCUMENTS

| | | | | |
|---|---|---|---|---|
| 1,559,114 A | * | 10/1925 | Maranville | A41D 19/01558 15/227 |
| 2,335,871 A | * | 12/1943 | Milligan | A61B 42/00 2/167 |
| 3,283,338 A | * | 11/1966 | Lucian | A41D 19/0062 2/161.6 |
| 5,323,490 A | * | 6/1994 | Yarbrough | A41D 19/0062 2/161.7 |
| 6,031,042 A | | 2/2000 | Lipinski | |
| 6,092,238 A | * | 7/2000 | Fierabend, Jr. | A41D 19/01564 2/16 |
| 6,451,893 B1 | | 9/2002 | Tao | |

(Continued)

OTHER PUBLICATIONS

Nick Gardner, Accelerator Free Fact or Fiction, Shield Scientific B.V., Health & Safety International, pp. 77-82, Oct. 2008.

(Continued)

*Primary Examiner* — Tejash Patel
(74) *Attorney, Agent, or Firm* — Sand & Sebolt (57) ABSTRACT

An ambidextrous or hand-specific glove including a wrist region, a palm region, and a digit region. The glove may be fabricated of nitrile rubber that is free of or essentially free of zinc, sulfur and accelerators to reduce allergic reactions in populations required to frequently wear protective gloves. A band region that partially or fully encircles a user's finger knuckles may be provided for easier finger bending. Texturing may be provided on glove surfaces that are used to grip articles. The tip regions on the front surface of the index and middle finger regions may be un-textured or smooth to enable a user to take a patient's pulse. These tip regions may be of reduced diameter and circumference so as to pull the glove material tightly around the tips of the user's finger so that even a faint pulse in a patient may be detected.

23 Claims, 8 Drawing Sheets

(56) References Cited

U.S. PATENT DOCUMENTS

| | | | | |
|---|---|---|---|---|
| 9,179,718 | B2* | 11/2015 | Anstey | A41D 19/015 |
| 2012/0036612 | A1* | 2/2012 | Hull | A41D 19/0003 |
| | | | | 2/163 |
| 2013/0239291 | A1* | 9/2013 | Harris | A41D 19/00 |
| | | | | 2/161.1 |
| 2017/0295868 | A1* | 10/2017 | Yahnite | A41D 19/0082 |

OTHER PUBLICATIONS

SemperSure™ Nitrile, www.sempermedusa.com/products/sempersure, Sempermed USA, Inc., 2 pages, document is undated but was publically available as of Aug. 18, 2014.

Nitrile Accelerator-Free Micro-Touch®, www.ansell.be/medical/pdf/gloves/EN/Micro-Touch%20Nitrile%20Accelerator-Free.pdf, Ansell, 2 pages, document is undated but was publically available as of Aug. 18, 2014.

Accelerator-Free Nitrile Exam Gloves—A Better Alternative, http://hourglass-intl.com/2011/04/18/accelerator-free-nitrile-exam-gloves-a-better-alternative/, Hourglass International, 4 pages, Apr. 18, 2011.

New Glove Materials Make Nitrile Gloves Better, http://hourglass-intl.com/2011/01/24/new-glove-materials-make-nitrile-gloves-better/, Hourglass International, 2 pages, Jan. 24, 2011.

* cited by examiner

PATTERNED MEDICAL GLOVE FOR USE WHEN TAKING A PULSE

CROSS-REFERENCE TO RELATED APPLICATIONS

This application is a Continuation of U.S. application Ser. No. 15/136,191 filed Apr. 22, 2016, which application claims the benefit of U.S. Provisional Application Ser. No. 62/152,302 filed Apr. 24, 2015, the disclosures of which are incorporated herein by reference in their entirety.

BACKGROUND OF THE INVENTION

Technical Field

The present invention relates generally to gloves and more particularly to nitrile gloves, such as those that may be used by medical professionals. Specifically, the present invention relates to a glove includes a first layer of nitrile rubber that is free of or essentially free of components that may cause hypersensitivity or allergic reaction in people who wear the glove. In particular, the nitrile rubber may be free of or essentially free of zinc and/or sulfur and/or accelerators and wherein an index finger region and/or middle finger region on the glove may be left un-textured or smooth to enable the user to easily take a patient's pulse.

Background Information

Nitrile or nitrile rubber gloves are well known in the art, such as for use in the medical field. One of the problems with such gloves is that some individuals have a hypersensitivity to various compounds that may be included in the gloves, such as zinc and/or sulfur and/or a variety of accelerators. Those accelerators may include but are not limited to components such as carbonates or thiurams. In addition, surgical or other gloves may have a tendency to stretch when worn for long periods of time, whereby the gloves may lose the ability to cling to the user's hand. This tendency for gloves to stretch may be a particular problem for surgeons.

SUMMARY

There is thus a need in the art for an improved glove for use by persons such as medical professionals that will have less of a tendency to affect or cause allergic reactions in persons with hypersensitivity to various components or compounds used in the production of nitrile gloves. Further, there is a need for gloves that are designed to allow medical professionals to take a pulse while also providing other desirable characteristics of the glove.

An ambidextrous glove and a hand-specific glove are disclosed herein. Each of the ambidextrous glove and the hand-specific gloves include a wrist region; a palm region; and a digit region. The wrist region, palm region and digit region define a hand-receiving cavity and the wrist region defines an opening to that hand-receiving cavity. The disclosed glove addresses some of the issues found with prior art gloves. The glove disclosed herein is comprised of at least a first layer of nitrile rubber that is free of or essentially free of zinc and/or sulfur and/or accelerators. Some accelerators that the glove's nitrile rubber may be free of or essentially free of may include carbonates or thiurams.

The composition of the disclosed glove may tend to reduce hypersensitivity or allergic reactions in populations that may be required to frequently wear protective gloves. The glove may include a band region in the digit region that partially encircles or fully encircles a user's knuckles in one or more of their fingers and thumb. These band regions make it easier for the user to bend their fingers and/or thumb while wearing the glove. This improved bendability provided by the glove may help improve the user's dexterity while wearing the glove. The presence of the band regions may also reduce the tendency of the glove material to become stretched when the glove is worn for a long period of time.

The disclosed glove may additionally be provided with texturing on surfaces that are used to grip articles such as the inside or front surfaces of the digit regions and the palm region. In such textured gloves the upper regions of the front surface on the index finger region and/or middle finger region may be left un-textured (i.e., texture-free) or smooth. The untextured or smooth front surfaces on the index and/or middle finger regions may enable the user to more easily take a patient's pulse than if these front surfaces were textured. The lack of texture helps ensure that the naturally-existing tactile sensitivity in the uppermost pads of the user's index finger and/or middle finger is as close as possible to how sensitive these regions of the user's fingers are if no gloves are being worn. If a patient has an extremely weak pulse or is unconscious, it is extremely common that the vast majority of EMT's (Emergency Medical Technicians) will immediately tear the index and middle finger regions off previously known gloves in order to expose their bare skin so that they may try and locate the patient's pulse. This tends to occur no matter what size glove the EMT is using. When it comes to taking a pulse, if there is any overlapping material on the middle or index finger regions of a glove, then that extra material tends to interfere with taking a pulse, particularly if the patient's pulse if faint. Of course, tearing the index and middle finger regions off a glove will leave the EMT at risk of contamination or harm because they now have exposed skin handling an injured or unconscious patient. The glove disclosed herein addresses this issue in that the smooth tip regions on the index finger region and middle finger regions ensure that there is close proximity between the user's fingertips and the patient's skin. In some embodiments, the fingertips of the glove of the present invention are of reduced circumference and diameter, thus ensuring the glove material is pulled tightly over the fingertips and ensuring that there is very little if any excess glove material that can interfere with the user finding a faint pulse on a patient.

In one aspect, the invention may provide a glove comprising a wrist region; a palm region extending outwardly from the wrist region; a digit region extending outwardly from the palm region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region are comprised of a first layer of nitrile rubber that is free of or essentially free of zinc and/or sulfur and/or accelerators.

In another aspect, the invention may provide a glove comprising a wrist region; a palm region extending outwardly from the wrist region; a digit region extending outwardly from the palm region, said digit region including an index finger region and middle finger region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region are comprised of at least a first layer of nitrile rubber that is free of or essentially free of one or more of zinc and/or sulfur and/or accelerators, and wherein the digit region and palm region may be textured except for a section of a front surface of one or both of the index finger region and the middle finger region and the section is located adjacent a tip of the associated index finger region and the middle finger region and extends for a distance downwardly therefrom and towards the palm region. The term "front section" should be understood to be that part of the index finger region or middle finger region that is adjacent the uppermost pad on the user's index or middle finger; where that uppermost pad is used to touch objects and is highly sensitive to the touch.

In another aspect, the invention may provide a glove comprising a wrist region; a palm region extending outwardly from the wrist region; a digit region extending outwardly from the palm region and comprising an index finger region, a middle finger region, a ring finger region, and little finger region and a thumb region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region are comprised of at least a first layer of nitrile rubber that is free of or essentially free of sulfur and one or more of the index finger region, middle finger region, ring finger region, little finger region and thumb region includes a band region adapted to be located proximate one or more of a user's finger knuckles; and the band region comprises alternating ridges and valley's formed in the first layer.

BRIEF DESCRIPTION OF THE SEVERAL VIEWS OF THE DRAWINGS

A sample embodiment of the invention is set forth in the following description, is shown in the drawings and is particularly and distinctly pointed out and set forth in the appended claims.

Similar numbers refer to similar parts throughout the drawings.

DETAILED DESCRIPTION

Figure 1:
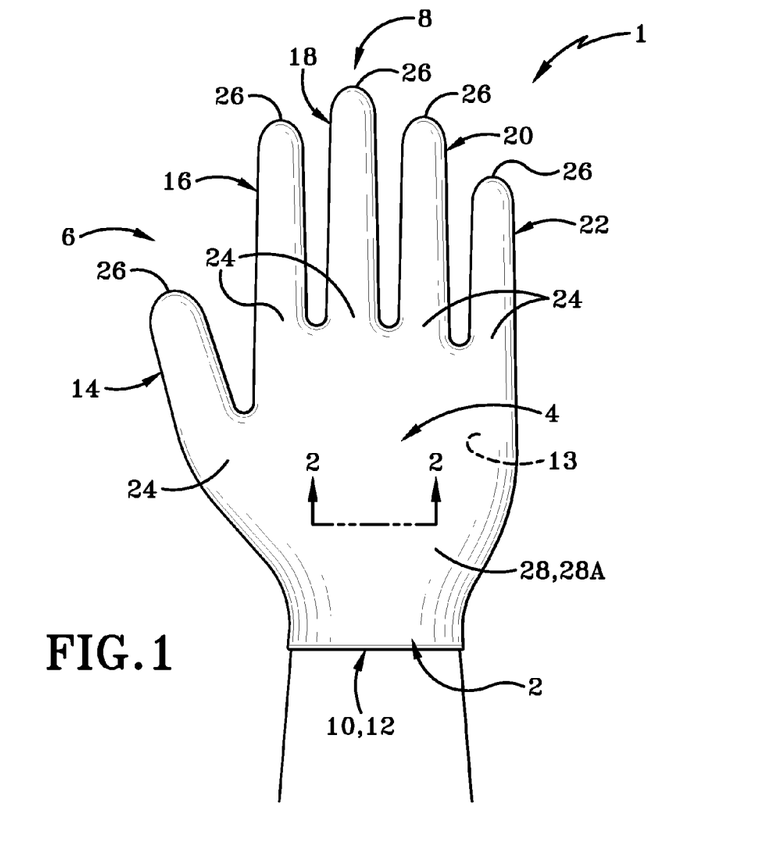
FIG. 1 is a front elevational view of a first embodiment of a glove in accordance with an aspect of the invention; where the glove is an ambidextrous glove and wherein a rear elevation view of the ambidextrous glove will be a mirror image of the glove shown in FIG. 1.

FIG. 1 shows a sample embodiment of an ambidextrous glove generally indicated at 1. Glove 1 includes a wrist region 2, a palm region 4 and a digit region 6. Glove 1 has a top 8 and a bottom 10 with a bottom entrance opening 12 of a hand-receiving cavity 13. Entrance opening 12 is at bottom 10 and serves to allow a user to insert his or her hand therethrough and into cavity 13. Entrance opening 12 is defined by wrist region 2. Cavity 13 extends from adjacent bottom 10 to adjacent top 8.

Digit region 6 includes five finger regions comprising a thumb region 14, an index region 16, a middle finger region 18, a ring finger region 20, and a little finger region 22. Each of the finger regions 14-22 has a base 24 and a tip 26. Each of the finger regions at its respective base 24 is secured to palm region 4 and extends upwardly and outwardly therefrom to the respective tip 26. Glove 1 has an outer surface 28 and an inner surface 30.

Figure 2:
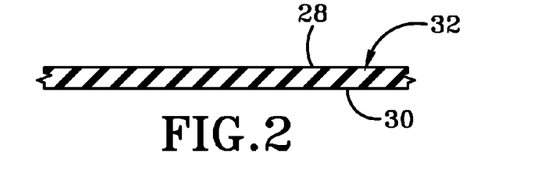
FIG. 2 is a cross-section of the front of the ambidextrous glove taken on line 2-2 of FIG. 1.
Figure 3:
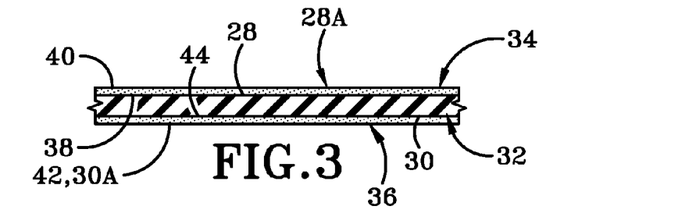
FIG. 3 is a cross-section of the front of the ambidextrous glove similar to FIG. 2 except showing an embodiment of the glove that includes additional layers in the glove.

Glove 1 may include a single first layer 32 as shown in FIG. 2, or a plurality of layers, such as layers 32, 34 and 36 as shown in FIG. 3. Where the single layer 32 is used, as shown in FIG. 2, outer surface 28 of glove 1 is also the outer surface of layer 32, and inner surface 30 of glove 1 is also the inner surface of layer 32.

Glove 1 may include one or more additional layers that make up the glove. FIG. 3 shows two additional layers used to form glove 1. In this particular example of a glove 1 with two additional layers, a second or intermediate layer 34 has inner and outer surfaces 38 and 40, and an outer or third layer 36 has inner and outer surfaces 42 and 44. Inner surface 38 of layer 34 may be in contact with and secured to outer surface 28 of first layer 32, while inner surface 42 of third layer 36 may be in contact with and secured to outer surface 40 of second layer 34. Thus, outer surface 44 of layer 36 serves as the outer surface 28A of glove 1 when formed of these three layers. Inner surface 30 in either case defines cavity 13 and extends from adjacent bottom 10 to adjacent top 8 and serves as the inner surface of wrist region 2, palm region 4 and each of the finger regions 14-22. Glove 1 may comprise one, two, three or more layers, as will be understood by those skilled in the art.

Where the single layer 32 is used, as shown in FIG. 2, outer surface 28 extends from adjacent bottom 10 to adjacent top 8 and serves as the outer surface of wrist region 2, palm region 4 and finger regions 14-22. Where the three layers are used as shown in FIG. 3, outer surface 44 or 28A extends from adjacent bottom 10 to adjacent top 8 and serves as the outer surface of wrist region 2, palm region 4 and finger regions 14-22.

Layer 32 may be formed of nitrile rubber. In particular, layer 32 may be formed of a nitrile rubber that is free of or essentially free of zinc and/or sulfur and/or accelerators. Thus, each of outer and inner surfaces 28 and 30 may be free of these same components and compounds, thereby providing a glove that reduces or essentially eliminates, in users, hypersensitivity or allergic reactions to compounds such as the zinc and/or sulfur and/or accelerators. It will be understood that people may have hypersensitivity to other compounds that may be used on occasion in nitrile gloves. It will be understood that the nitrile gloves in accordance with an aspect of the present invention may be free of or essentially free of compounds that cause hypersensitivity or allergic reactions in users who wear the glove 1.

In the case of glove 1 which includes more than one layer; layer 32 may likewise be formed of this same nitrile rubber that is free zinc and/or sulfur and/or accelerators. Layers 34 and 36 may be formed of various types of polymers that are typically elastomeric polymers that are different from layer 32 and which may be the same as or different from one another. Thus, the elastomeric polymer of any of the additional layers may have a different composition to the nitrile rubber used in the first layer. The layers other than inner layer 32 may be formed of polymers that may or may not include zinc and/or sulfur and/or an accelerator. The use of an additional polymer layer or layers to define outer surface 28A thus may provide a multilayer glove that essentially eliminates the allergic reaction to compounds such as the zinc and/or sulfur and/or accelerators noted above for a person having hypersensitivity to such elements or compounds. This may be true even if the outer layer includes zinc and/or sulfur and/or an accelerator because allergic reactions of this nature are most commonly caused by prolonged contact with the allergen such as when a person wears the glove for an extended period so that contact of the wearer's hand and the inner layer/surface of the glove is the primary concern related to producing allergic reactions.

Figure 4:
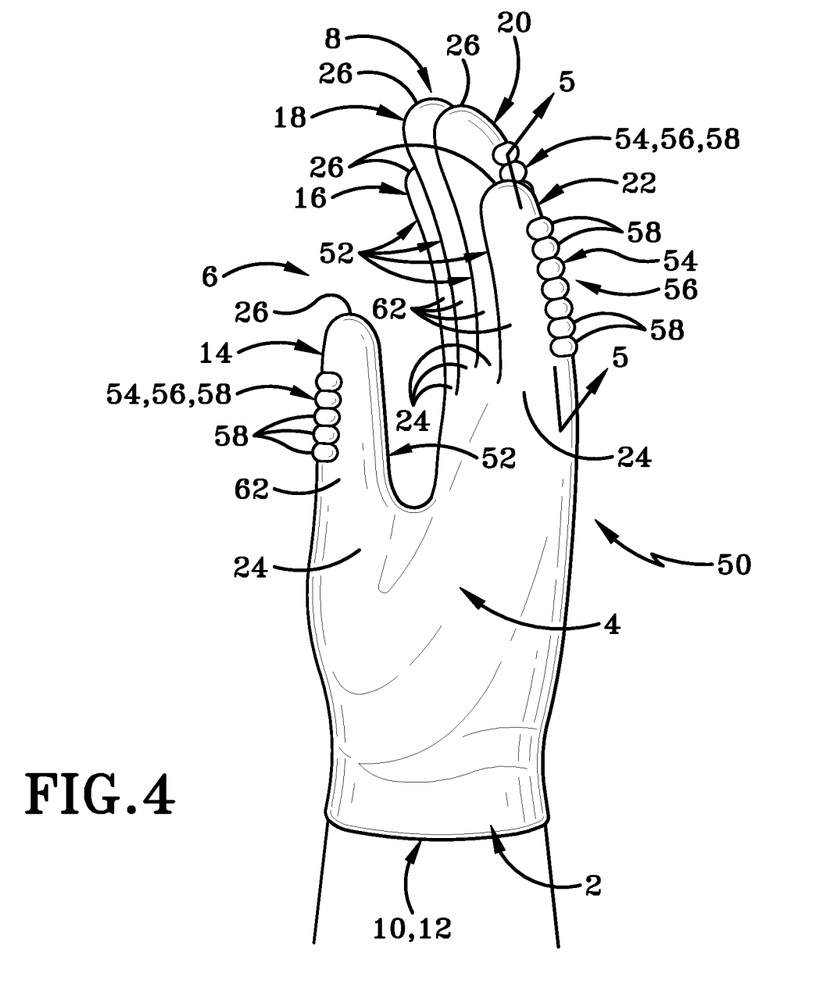
FIG. 4 is a side elevational view of a second embodiment of the glove in accordance with the present invention showing a hand specific glove for a right hand; wherein the left handed glove will be a mirror image hereof; and wherein the glove includes a plurality of band regions formed in the digit regions.

Referring now to FIG. 4, a glove 50 is shown that is a hand-specific glove. In particular, FIG. 4 shows a right-handed glove although it will be understood that FIG. 4 should likewise represent a left-handed glove inasmuch as a left-handed glove is a mirror image of that shown in FIG. 4. Thus, unlike the ambidextrous glove 1 shown in FIG. 1 in which all of the finger regions including thumb region 14 are aligned along or intersected by a common plane, glove 50 is configured such that the four finger regions 16, 18, 20 and 22 may be aligned along a common plane whereas thumb region 14 is spaced from said plane. Aside from the fact that glove 50 is a hand-specific glove, it is nonetheless similar to glove 1 in that it includes a wrist region 2, a palm region 4, and a digit region 6 which includes five finger regions comprising a thumb region 14, index finger region 16, middle finger region 18, ring finger region 20 and little finger region 22. FIG. 4 also shows that each of the finger regions 14-22 has a base 24 and a tip 26 and is secured to palm region 4 as described with respect to glove 1. Each of finger regions 14-22 has a finger front 52 and a finger back 54. It is noted that the finger fronts 52 of finger regions 16-22 generally face in the same direction and that the finger backs 54 of finger regions 16-22 face generally in the same direction and the opposite direction as finger fronts 52 thereof. On the other hand, the finger front 52 of thumb region 14 faces in a different direction than that of the finger fronts 52 of the index, middle, ring and the little finger regions 16-22 and the finger back 54 of thumb region 14 likewise faces in a different direction than that of finger backs 54 of finger regions 16-22.

One or more of each of finger regions 14-22 along the finger back 54 thereof may include a band region 56 including a plurality of band segments 58 that include respective elastomeric bands 60. Each band region 56 also includes a plurality of trough segments 64 between each adjacent pair of band segments 58. In the sample embodiment, the top of the band region 58 of a given finger region may be spaced downwardly a distance from the tip 26 of the given finger region, for instance, about ½ or ¾ inch to about ¾, 1 or 1¼ inch and therefore may be positioned between a tip of the user's finger and the user's first knuckle in that finger. The bottom of each band region 58 may be located so that the bottom is located between the user's palm and lowermost knuckle on that particular finger or thumb (obviously only one knuckle is located on the thumb and the band region 58 associated therewith will originate between the tip and the knuckle and the bottom of the band region will fall between the user's palm and knuckle on the thumb. Each finger region 14-22 is formed of a peripheral wall 62 that defines the respective finger front and back 52 and 54, including the respective band region 56 of band segments 58 and trough segments 64.

Figures 5, 6:
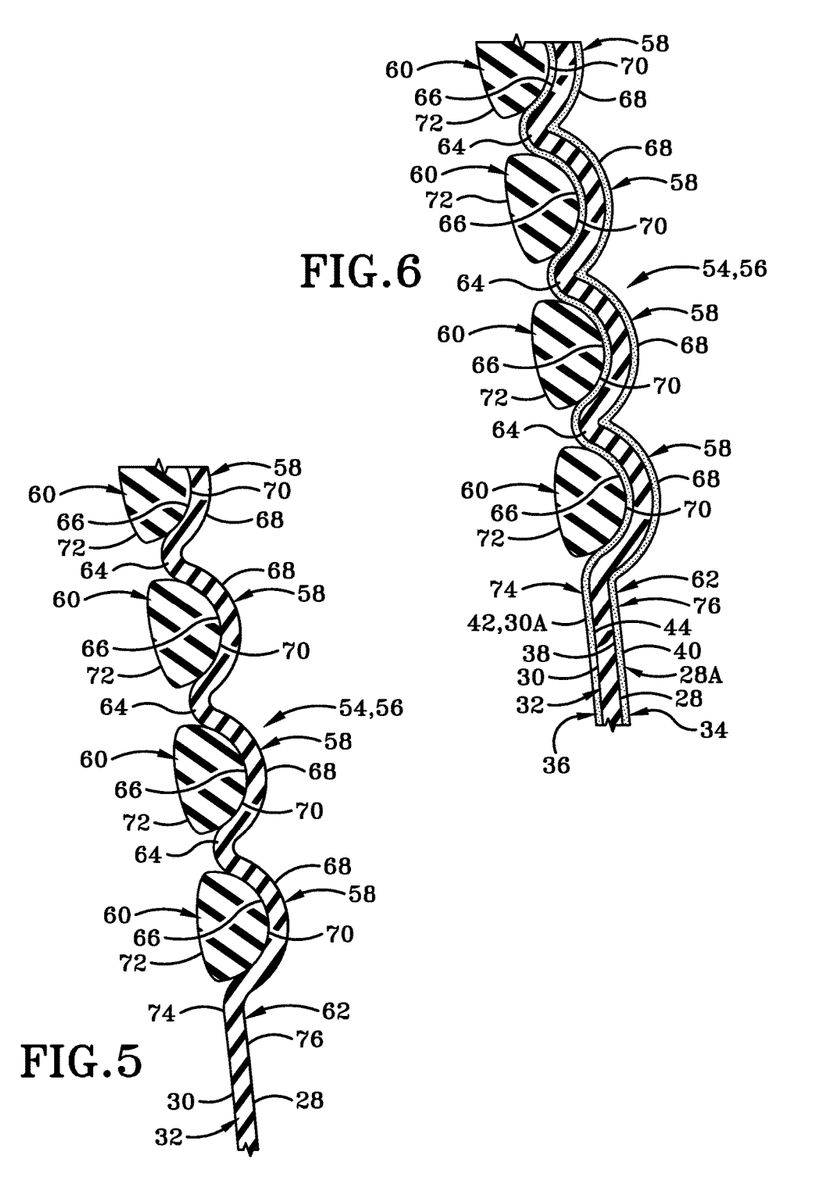
FIG. 5 is a cross-sectional view of the glove taken on line 5-5 of FIG. 4.
FIG. 6 is a cross-sectional view similar to FIG. 5 but showing additional layers of the glove.

With reference to FIGS. 5 and 6, band region 56 is described in this paragraph as viewed in a section view taken parallel to the longitudinal axis of the given finger region. Each band segment 58 has a concavely curved inner surface 66 and a convexly curved outer surface 68 such that surfaces 66 and 68 extend from adjacent the top of the given band segment 58 to adjacent the bottom of the given band segment 58. Inner surface 66 faces the longitudinal axis of the given finger region and the portion of cavity 13 defined by the given finger region while outer surface 68 faces away from the longitudinal axis of the given finger region and the portion of cavity 13 defined by the given finger region. For a given pair of adjacent band segments 58, the top of the lower band segment (including its surfaces 66 and 68) is adjacent the trough segment 64 between the given adjacent pair and the bottom of the higher band segment (including its surfaces 66 and 68), which is also adjacent the trough segment 64 between the given adjacent pair. Each band 60 has a convexly curved outer surface 70 and an inner surface 72. Each of surfaces 70 and 72 extend from adjacent the top of the given band 60 to the bottom of the given band 60. Inner surface 72 faces the longitudinal axis of the given finger region and the portion of cavity 13 defined by the given finger region while outer surface 70 faces away from the longitudinal axis of the given finger region and the portion of cavity 13 defined by the given finger region. Outer surface 70 of a given band is in contact with and secured to the inner surface 66 of a given band segment 58.

Each band 60 is curved as viewed from above or parallel to the longitudinal axis of the given finger region so that inner surface 72 is concavely curved and outer surface 70 is convexly curved as so viewed. Each band 60 is thus configured to partially wrap around the back of a given finger of a person wearing glove 50 with the given inner surface 72 contacting the back of the given finger. This configuration helps prevent glove 50 from sliding off of the person's hand, especially when worn over an extended period of time. Each band 60 in the sample embodiment extends only along the finger back 54 of a given finger region, and thus no portion of band 60 extends along the finger front 52 of the given finger region. The band regions 58 stretch or elongate when the user bend their finger regions 14-22 and elastically returns to the region's original configuration when the finger region 14-22 is straightened. Band regions 58 aid in reducing the forces applied to the finger regions 14-22 and thus tend to reduce the degree to which the finger regions may stretch over time.

As with the multilayer version of glove 1 in FIG. 3, where additional layers are used for glove 50 as shown in FIG. 6, the second or intermediate layer 34 has inner and outer surfaces 38 and 40, and the outer or third layer 36 has inner and outer surfaces 42 and 44. Inner surface 38 of layer 34 is in contact with and secured to outer surface 28 of first layer 32, while inner surface 42 of third layer 36 is in contact with and secured to outer surface 40 of second layer 34. Thus, outer surface 44 of layer 36 serves as the outer surface 28A of glove 50 when formed of these three layers. Inner surface 30 in either case defines cavity 13 and extends from adjacent bottom 10 to adjacent top 8 and serves as the inner surface of wrist region 2, palm region 4 and each of the finger regions 14-22. Where the single layer 32 is used as shown in FIG. 2, outer surface 28 extends from adjacent bottom 10 to adjacent top 8 and serves as the outer surface of wrist region 2, palm region 4 and finger regions 14-22. Where the three layers are used as shown in FIG. 3, outer surface 44 or 28A extends from adjacent bottom 10 to adjacent top 8 and serves as the outer surface of wrist region 2, palm region 4 and finger regions 14-22.

Peripheral wall 62 is formed entirely from layer 32 in a single layer version of glove 50 (FIGS. 4, 5) and may be formed by a plurality of layers, such as layers 32, 34 and 36 in a multilayer version of glove 50 (FIGS. 4, 6). Thus, for the single layer version or multilayer version, inner surface 30 includes a finger region inner surface or peripheral wall inner surface 74 of a given finger region 14-22 or peripheral wall 62. For the single layer version, outer surface 28 includes a finger region outer surface or peripheral wall outer surface 76 of a given finger region 14-22 or peripheral wall 62. For the multilayer version, outer surface 28A/44 includes a finger region outer surface or peripheral wall outer surface 76 of a given finger region 14-22 or peripheral wall 62.

Layers 32, 34 and 36 of glove 50 are formed of the same materials as noted above with respect to glove 1, and each band 60 is formed of a nitrile rubber that is free of or essentially free of zinc and/or sulfur and/or accelerators. Thus, layer 32 and bands 60 provide the same hypoallergenic qualities noted above.

Figure 7:
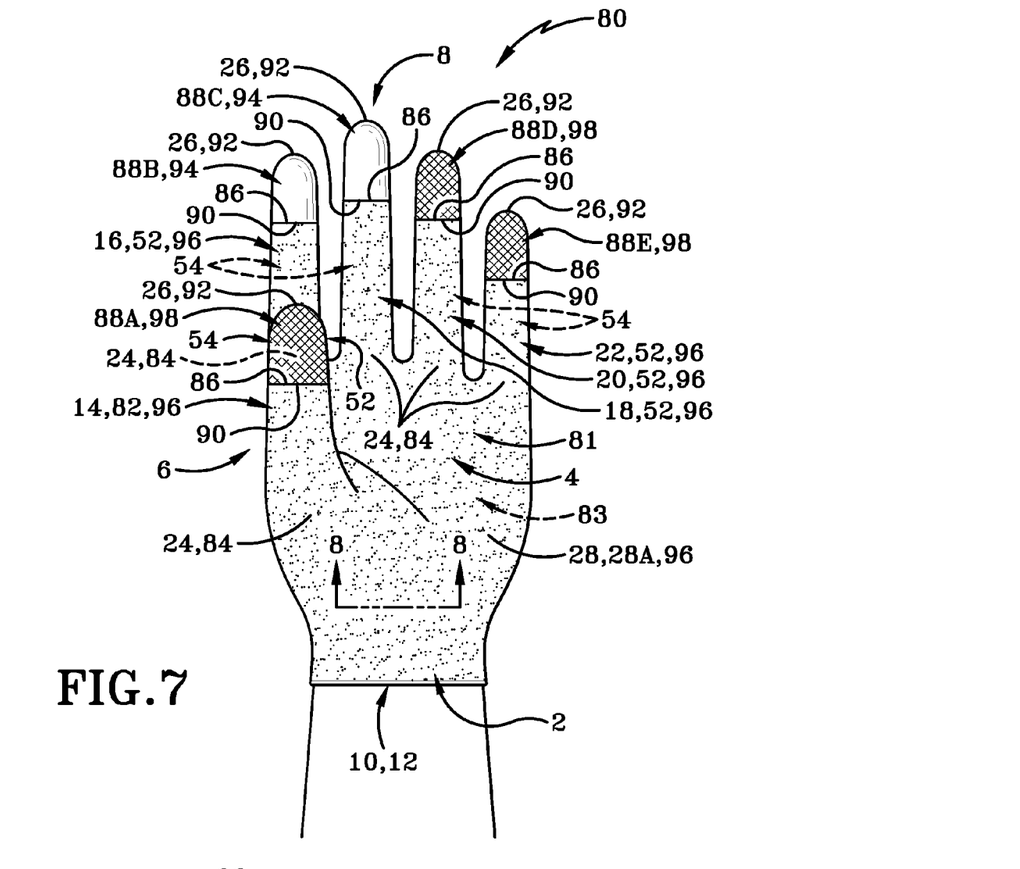
FIG. 7 is a front elevational view a third embodiment of a glove in accordance with an aspect of the invention; where the glove illustrated is a hand-specific glove for a user's left-hand; wherein a right hand hand-specific glove would be a mirror image hereof; and wherein the figure shows texturing on the palm and digit regions but not on the front surfaces of tip regions on the index finger region and the middle finger region.

Referring now to FIG. 7, a glove 80 is shown that is a hand-specific glove. In particular, FIG. 7 shows a left-handed glove although it will be understood that FIG. 7 should likewise represent a right-handed glove inasmuch as a right-handed glove is a mirror image of that shown in FIG. 7. Thus, glove 80 is configured such that the four finger regions 16, 18, 20 and 22 may be aligned along a common plane whereas thumb region 14 is spaced from said plane. Glove 80 includes a wrist region 2, a palm region 4, and a digit region 6 that includes five finger regions comprising a thumb region 14, index finger region 16, middle finger region 18, ring finger region 20 and little finger region 22.

FIG. 7 also shows that each of finger regions 14-22 has a base 24 and a tip 26 and is secured to palm region 4 as described with respect to glove 1. Glove 80 has a front or front side 81 (or palm side) and a back or back side 83.

Each of finger regions 14-22 has a finger front 52 and a finger back 54. The finger fronts 52 of finger regions 16-22 generally face in the same direction and that the finger backs 54 of finger regions 16-22 face generally in the same direction and the opposite direction as finger fronts 52 thereof. On the other hand, the finger front 52 of thumb region 14 faces in a different direction than that of the finger fronts 52 of the index, middle, ring and the little finger regions 16-22 and the finger back 54 of thumb region 14 likewise faces in a different direction than that of finger backs 54 of finger regions 16-22. Each finger region 14-22 is formed of a peripheral wall 62 that defines the respective finger front and back 52 and 54.

Each of finger regions 14-22 has a finger base region 82 having a bottom 84 adjacent the respective base 24 and a top 86. Each of finger regions 14-22 has a fingertip region 88 that extends upwardly from the corresponding base region 82 to adjacent the corresponding tip 26. Each fingertip region 88 has a bottom 90 at or adjacent the corresponding top 86 and a top 92 at or adjacent the corresponding tip 26. Fingertip regions 88 may include fingertip region 88A of thumb region 14, fingertip region 88B of index finger region 16, fingertip region 88C of middle finger region 18, fingertip region 88D of ring finger region 20, and fingertip region 88E of little finger region 22.

In the sample embodiment, the fingertip region bottom 90 and finger base top 86 of a given finger region 14-22 is spaced downwardly a distance from the fingertip region top 92 and tip 26 of the given finger region, for instance, about ½ or ¾ inch to about ¾, 1 or 1¼ inch. Thus, each fingertip region 88 may have a height from bottom 90 to top 92 of about ½ or ¾ inch to about ¾, 1 or 1¼ inch. Each finger base region 82 and fingertip region typically extends along the finger front 52 of the given finger region and may also extend along the corresponding finger back 54.

Whereas gloves 1 and 50 typically have an outer surface that is smooth in its entirety, glove 80 may have an outer surface that may have smooth portions and textured portions. In the sample embodiment, the outer surface of glove 80 has one or more smooth outer surfaces 94, one or more lighter textured outer surfaces 96 that are coarser than smooth surface 94, and one or more even coarser textured outer surfaces 98 that are coarser than smooth surface 94 and lighter textured surface 96. Fingertip region 88B of index finger region 16 and fingertip region 88C of middle finger region 18 may have smooth outer surfaces 94 that extend from adjacent the corresponding bottom 90 to adjacent the corresponding top 92. Bottom 90 is located in a region that may be approximately positioned adjacent a front of the first knuckle on a user's hand. Smooth surface 94 extends from top 92 of index finger region 52 and middle finger region 54 downwardly for approximately a third of the total length of index finger region 52 and middle finger region 54. (The length will be understood to extend from the tip of any particular finger region to the palm region of the glove.) Smooth surface 94 may be confined to extend only along the given finger front 52 or may also extend along the given finger back 54.

Fingertip region 88A of thumb region 14, fingertip region 88D of ring finger region 20 and fingertip region 88E of little finger region 22 may have coarser textured outer surfaces 98 that extend from adjacent the corresponding bottom 90 to adjacent the corresponding top 92. Coarser textured surface 98 may be confined to extend only along the given finger front 52 or may also extend along the given finger back 54.

The finger base region 82 of each of thumb region 14, index finger region 16, middle finger region 18, ring finger region 20 and little finger region 22 may have lighter textured outer surfaces 96 that extend from adjacent the corresponding bottom 84 to adjacent the corresponding top 86. Lighter textured surface 96 may be confined to extend only along the given finger front 52 or may also extend along the given finger back 54.

Wrist region 2 and palm region 4 may have lightly textured outer surfaces 96 that extend only along front side 81 of glove 80 or which may also extend along back side 83. Lightly textured outer surface 96 may extend along the entirety of wrist region 2 along front side 81 and may extend along the entirety of wrist region 2 along back side 83. Lightly textured outer surface 96 may extend along the entirety of palm region 4 along front side 81 and may extend along the entirety of palm region 4 along back side 83. Typically, lightly textured outer surface 96 extends from adjacent the top of wrist region 2 to adjacent the base 24 of each of finger regions 14-22 along front side 81.

Figure 8:
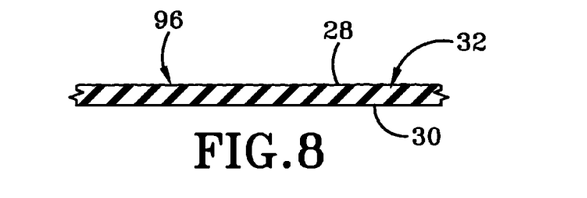
FIG. 8 is a cross-sectional view of the glove taken along line 8-8 of FIG. 7.
Figure 9:
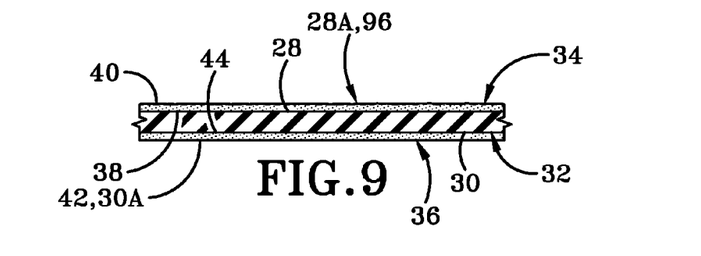
FIG. 9 is a cross-sectional view of the glove similar to FIG. 8 showing additional layers of the glove.

As with the multilayer version of glove 1 in FIG. 3 and glove 50 in FIG. 6, where additional layers are used for glove 80 as shown in FIG. 9, the second or intermediate layer 34 has inner and outer surfaces 38 and 40, and the outer or third layer 36 has inner and outer surfaces 42 and 44. Inner surface 38 of layer 34 is in contact with and secured to outer surface 28 of first layer 32, while inner surface 42 of third layer 36 is in contact with and secured to outer surface 40 of second layer 34. Thus, outer surface 44 of layer 36 serves as the outer surface 28A of glove 80 when formed of these three layers. Inner surface 30 in either case defines cavity 13 and extends from adjacent bottom 10 to adjacent top 8 and serves as the inner surface of wrist region 2, palm region 4 and each of the finger regions 14-22. Where the single layer 32 is used as shown in FIG. 8, outer surface 28 extends from adjacent bottom 10 to adjacent top 8 and serves as the outer surface of wrist region 2, palm region 4 and finger regions 14-22. Where the three layers are used as shown in FIG. 9, outer surface 44 or 28A extends from adjacent bottom 10 to adjacent top 8 and serves as the outer surface of wrist region 2, palm region 4 and finger regions 14-22.

Peripheral wall 62 is formed entirely from layer 32 in a single layer version of glove 80 (FIGS. 7, 8) and may be formed by a plurality of layers, such as layers 32, 34 and 36 in a multilayer version of glove 80 (FIGS. 7, 9). Outer surface 28 in the single layer version thus includes the smooth, lighter textured and coarser textured surfaces 94, 96 and 98, whereas outer surface 28A/44 in the multilayer version includes the smooth, lighter textured and coarser textured surfaces 94, 96 and 98. Layers 32, 34 and 36 of glove 80 are formed of the same materials as noted above with respect to glove 1 so that layer 32 provides the same hypoallergenic qualities noted above. The textured surfaces provided on glove 80 may be provided on regions of glove 80 that will be contacted when an article is gripped when glove 80 is worn by a user. The textured surfaces will, thus, enhance the gripping ability of the user and reduce the tendency for objects to slip when being held by the user when wearing glove 80.

Figure 10:
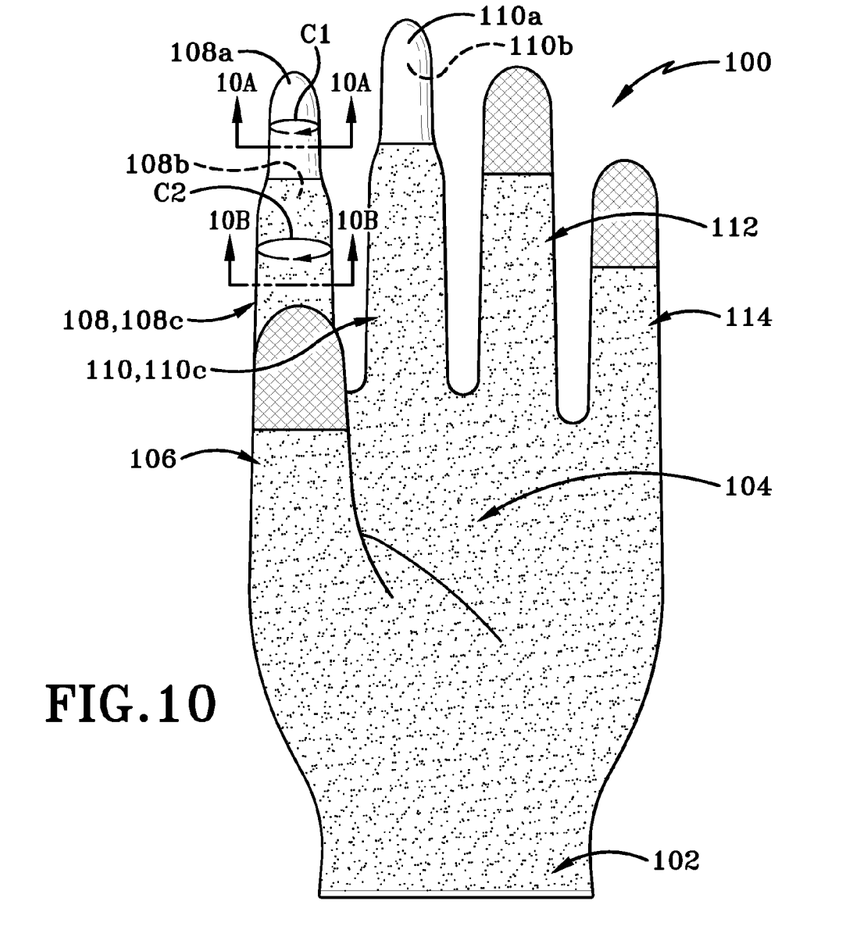
FIG. 10 is a front elevational view of a fourth embodiment of a glove in accordance with an aspect of the present invention, where the glove is a hand specific glove and the tip regions of the index and middle finger regions are of a reduced circumference and diameter.
Figure 10A:
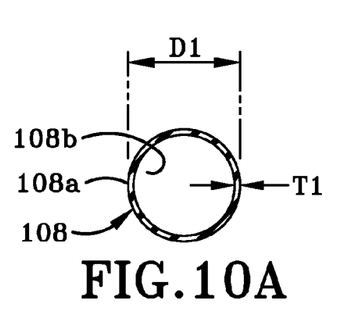
FIG. 10A is a cross-section through the tip region of the index finger region of the glove shown in FIG. 10.
Figure 10B:
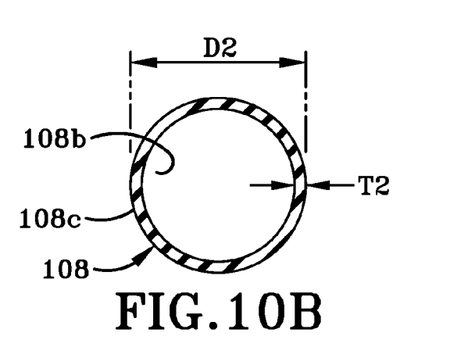
FIG. 10B is a cross-section through a wider portion of the index finger region of the glove of FIG. 10, where the wider portion is located below the tip region.

Referring to FIGS. 10-10B there is shown a fourth embodiment of a glove in accordance with an aspect of the invention, generally indicated at 100. Glove 100 includes a wrist region 102, a palm region 104, a thumb region 106, an index finger region 108, a middle finger region 110, a ring finger region 112, and a little finger region 114. Glove 100 is illustrated as a hand-specific glove but the same principles as will be discussed hereafter may be incorporated into an ambidextrous glove.

Glove 100 may be substantially identical to any of the gloves 1, 50, or 80 except that at least the tip region 108a, 110a of the index finger region 108 and the middle finger region 110 are fabricated to be of a smaller circumference and diameter than are the tip regions of the index finger regions and middle finger regions of any of the other glove embodiments disclosed herein. Additionally the tip regions 108a, 110a of the index and ring finger regions 108, 110 are of a smaller circumference and diameter than the remaining length of the respective one of the index and middle finger regions 108, 110. The remaining length of these two finger regions is represented by the reference numbers 108c and 110c, respectively in FIG. 10. Furthermore, the tip regions 108a, 110a are smaller in diameter and circumference than the ring finger region 112, little finger region 114 and thumb region 106 of glove 100. The circumference of the tip regions 108a, 110a is measured around an exterior surface of the respective index finger region 108 or middle finger region 110 and in an orientation at right angles to the length of the respective finger region 108 or 110. The length is measured from a tip of the respective finger region down to the palm region 104. The reduced dimensions (i.e., circumference and diameter) ensure that the glove material in each tip region 108a, 110a is pulled tightly around the user's index and middle fingers. The tightly pulled material or film of glove 100 ensures that the user can more easily and readily locate a faint pulse in a patient than if the glove material was only fitted loosely around these two fingertips.

The dimensions of the tip region 108a of the index finger region and the tip region 110a of the middle finger region 110 may be reduced by from about 10% up to about 20% relative to the remaining length of that particular finger region 108 or 110, and to the other finger regions 112, 114 and thumb region 106 in glove 100, or to the finger regions of any of the other embodiments of the glove, and relative to finger regions in prior art gloves. This reduction in the dimensions of the tip regions helps ensure that the glove film/material is stretched to the point that the film/material fits tightly against the user's index and middle fingers. The film needs to be pulled tight enough to ensure that even a faint pulse may be detected through the film but the film should not be stretched so tight that the gloves are restrictive or uncomfortable to wear.

Instead of just the tip regions 108a, 110a being of a smaller diameter "D1" and circumference "C1" relative to the tip regions of the other finger regions of the gloves disclosed herein, substantially all of the tip regions of the finger regions on glove 100 (including the thumb region 106, ring finger region 112 and little finger region 114) may be fabricated to be of a reduced diameter and circumference relative to the remaining lengths of those finger regions. Still further, instead of just the tip regions 108a, 110a being of smaller diameter and circumference, the entire index finger region 108 and entire middle finger region 110 may be fabricated to have smaller dimensions relative to the index finger region and middle finger regions of the other embodiments of the glove disclosed herein and relative to the ring finger region 112, little finger region 114 and thumb region 106 of glove 100. In other words, the index finger region 108 and 110 may be of smaller diameter and circumference along substantially the entire length thereof from the palm region to the tip of the respective finger region instead of only being smaller in dimension along the tip region 108a or 110a.

Referring to FIGS. 10 and 10A, there is shown a cross-section through tip region 108a of index finger region 108. Tip region 108a is shown to have a circumference "C1" measured around an exterior surface of the tip region 108a; and a diameter "D1". The circumference "C1" is of such a size that when glove 100 is donned, the tip region 108a will be smaller than the circumference and diameter of the user's finger that is received in the interior cavity 108b thereof. Because of this reduced circumference "C1", the film of index finger region 108 will be pulled tightly around the user's finger as the material thereof stretches to allow of the user's index finger to enter into the interior 108b thereof. Because of the stretching of the film of tip region 108a to accommodate the user's index finger, the thickness of the wall of tip region 108a will be reduced to a thickness "T1". (A similar situation exists with tip region 110a when the user's middle finger is inserted into the interior 110b therein.) FIG. 10B shows a cross-section through the wider part 108c of the index finger region 108. This wider part 108c is located below the tip region 108a. The circumference of the wider part 108c is greater than the circumference "C1" of the tip region 108a and is indicated in FIG. 10B as circumference "C2". The wider part 108c is of a diameter "D2" that is greater than the diameter "D1" of tip region 108a. The circumference "C2" is of a size that will be greater than the diameter of a user's index finger that will be received into the interior 108b of index finger region 108. The thickness "T2" of the wall of wider part 108c is greater than the thickness "T1" of the wall of tip region 108a. The thinner wall thickness "T1" of index finger region 108 ensures that the material of the tip region 108a is pulled tighter around the tip of the user's finger than is the material along the rest of the length of the wider part 108b.

Figure 10C:
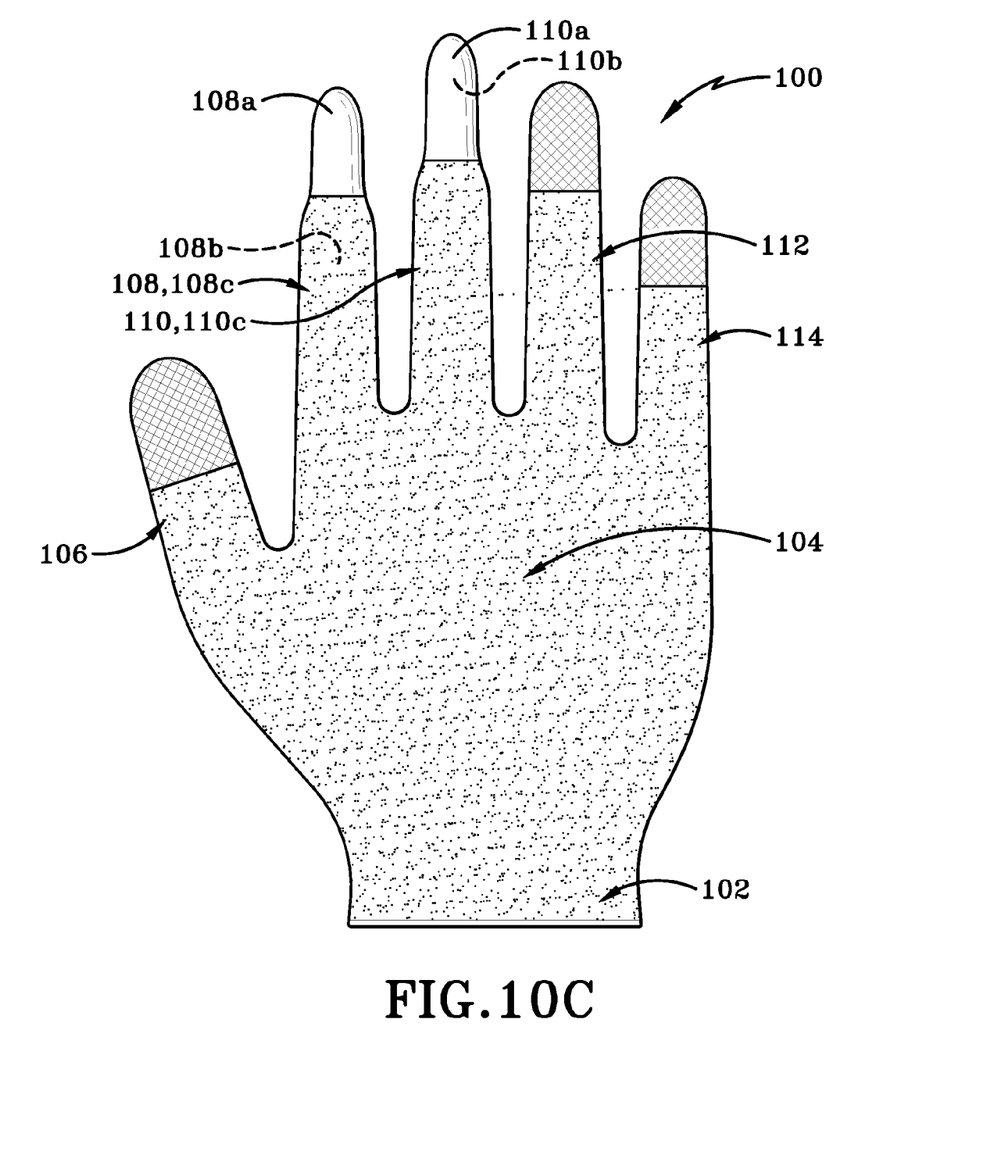
FIG. 10C is a front elevation view of the fourth embodiment of the glove shown as an ambidextrous glove.

FIG. 10 shows that tip regions 108a, 110a are smooth or free of texture, i.e., un-textured, thereby hindering the tactile sensitivity of the user's fingertips on their index and middle fingers to a lesser extent than if the tip regions 108a, 110a were textured. FIG. 10C is a front elevation view of the fourth embodiment of the glove. In this instance, the glove 100 is an ambidextrous glove instead of a hand specific glove. It will be understood that the rear elevation view of this glove will be a mirror image of what is illustrated in FIG. 10C.

Figure 11:
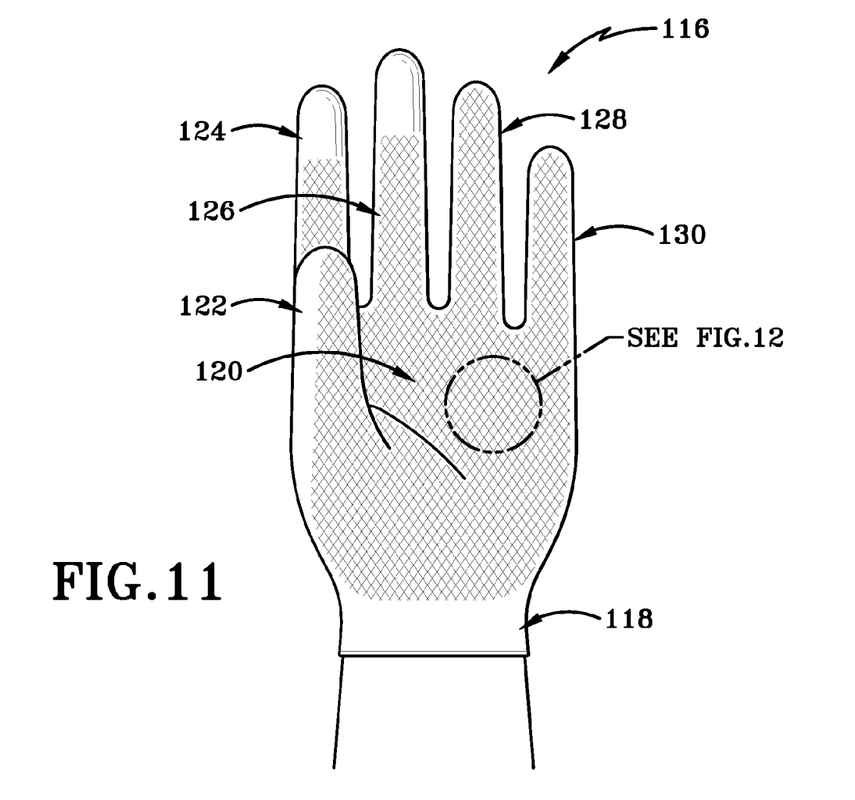
FIG. 11 is a front elevational view of a fifth embodiment of a glove in accordance with another aspect of the present invention, where the glove is a hand specific glove that has texturing on the gripping surfaces of the glove but where the tip regions of the index finger region and middle finger region are free of texturing and are smooth.
Figure 12:
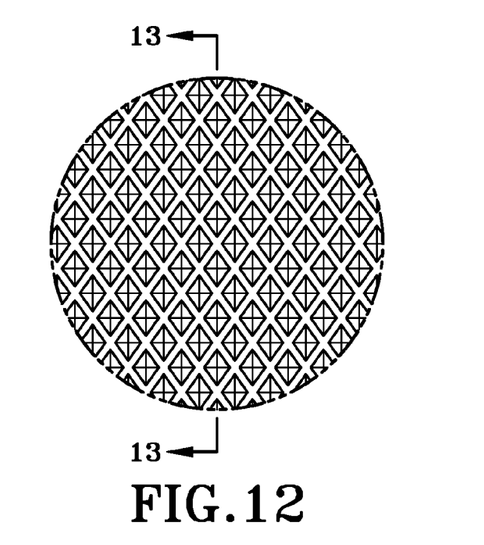
FIG. 12 is an enlargement of the highlighted region of FIG. 11 showing the diamond texture pattern.
Figure 13:
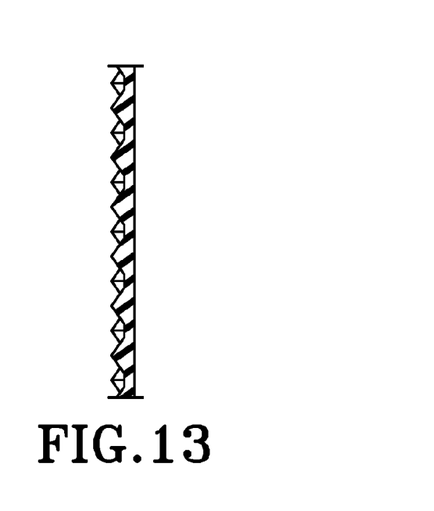
FIG. 13 is a cross-section taken along line 13-13 of FIG. 12 and showing the diamond texture pattern in greater detail.

Referring now to FIGS. 11-13, there is shown a fifth embodiment of a glove in accordance with an aspect of the invention, generally indicated at 116. Glove 116 includes a wrist region 118, a palm region 120, a thumb region 122, an index finger region 124, a middle finger region 126, a ring finger region 128, and a little finger region 130. Glove 116 is illustrated as a hand-specific glove but the same principles as will be discussed hereafter may be incorporated into an ambidextrous glove.

Glove 116 may be substantially identical to any of the gloves 1, 50, 80 or 100 particularly as relating to the shape and features of these gloves. Glove 116 differs from the other gloves disclosed herein in that substantially the entire front surface of the glove, i.e., the gripping surfaces thereof, is textured except for the smooth and un-textured tip regions 124a and 126a in index finger region 124 and middle finger region 126. The rear surface and/or side surfaces of the glove 116 may also be textured if that is desired or if the glove is an ambidextrous glove.

The texture pattern utilized in glove 116 has been found to be most advantageous if the pattern is a diamond pattern. The illustrated diamond pattern allows for better gripping ability when wearing glove 116 because of the additional friction provided by the raised diamond shapes on the glove's exterior surface. The diamond shapes in the pattern also effectively and efficiently wick water and other liquids away from the glove's exterior surface. This again improves the gripping ability of the exterior surface of the glove 116. It will be understood that instead of using a diamond pattern, other patterns may be utilized on glove 116.

Figure 11A:
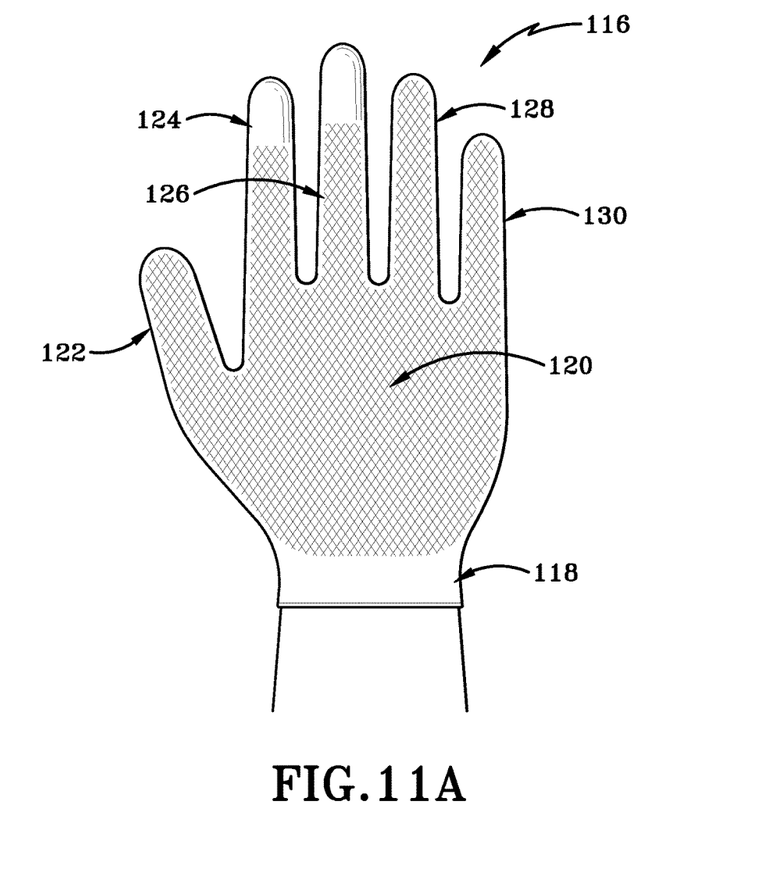
FIG. 11A is a front elevation view of the fifth embodiment of the glove shown as an ambidextrous glove.

FIG. 11A is a front elevation view of the fifth embodiment of the glove 116 except that, in this instance, the glove 116 is an ambidextrous glove. It will therefore be understood that the rear elevation view of glove 116 will be a mirror image of what is illustrated in FIG. 11A.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration set out herein are an example and the invention is not limited to the exact details shown or described.

The invention claimed is:

1. A glove comprising:
   a wrist region;
   a palm region extending outwardly from the wrist region;
   a thumb region, an index finger region, a middle finger region, a ring finger region and a little finger region all extending outwardly from the palm region and wherein the glove comprises of a layer of material that forms at least an outer surface of the glove; and wherein the thumb region, the index finger region, the middle finger region, the ring finger region and the little finger region each have a tip region and a remaining portion and wherein the tip region has a front surface and the remaining portion has a front surface; wherein the tip region extends from proximate a tip of a respective one of thumb region, the index finger region, the middle finger region, the ring finger region and the little finger region to proximate where a first knuckle of a user's thumb or finger will be located when the glove is worn; and the remaining portion extends from where the first knuckle of the user's thumb or finger will be located when the glove is worn, down to the palm region;
   wherein the front surface of the tip region of the index finger region is free of texture; and
   wherein the front surface of the remaining portion of the index finger region is textured.

2. The glove as defined in claim 1, wherein the texture is provided by a diamond-shaped pattern that is formed in the layer of material.

3. The glove as defined in claim 2, wherein the diamond-shaped pattern is a raised pattern that provides a contoured exterior surface to the remaining portion of the index finger region.

4. The glove as defined in claim 1, wherein the layer of material in the tip region of the middle finger region has a front surface that is free of texture; and
   wherein the layer of material in the remaining portion of the middle finger region has a texture formed therein; and the texture is on a front surface of the remaining portion.

5. The glove as defined in claim 4, wherein the texture is provided by a diamond-shaped pattern formed in the layer of material.

6. The glove as defined in claim 5, wherein the diamond-shaped pattern is a raised pattern that provides a contoured exterior surface to the remaining portion of the middle finger region.

7. The glove as defined in claim 1, wherein the layer of material in each of the ring finger region and little finger region has texture formed therein and the texture is provided on a front surface and from proximate the tip of ring finger region to the palm region and from the tip of the little finger region to proximate the palm region.

8. The glove as defined in claim 7, wherein the texture on the ring finger region and the little finger region is provided by a diamond-shaped pattern formed in the layer of material.

9. The glove as defined in claim 8, wherein the diamond-shaped pattern is a raised pattern that provides a contoured exterior surface to each of the ring finger region and the little finger region.

10. The glove as defined in claim 7 the layer of material in one or more of the thumb region, the palm region and the wrist region has texture formed therein.

11. The glove as defined in claim 10, wherein the texture in the layer of material in the one or more of the thumb region, the palm region and the wrist region is provided by a diamond-shaped pattern.

12. The glove as defined in claim 11, wherein the diamond-shaped pattern is a raised pattern that provides a contoured exterior surface to each of the one or more of the thumb region, the palm region and the wrist region.

13. The glove as defined in claim 1, wherein the glove is an ambidextrous glove and the thumb region, index finger region, middle finger region, ring finger region, and little finger region are all aligned along a common plane.

14. The glove as defined in claim 1, wherein the glove is a hand-specific glove having the index finger region, middle finger region, ring finger region, and little finger region are all aligned along a common plane and the thumb region spaced from said common plane.

15. A glove comprising:
    a wrist region;
    a palm region extending outwardly from the wrist region;
    a thumb region, an index finger region, a middle finger region, a ring finger region and a little finger region all extending outwardly from the palm region and each having a tip region and a remaining portion, where the tip region extends from proximate a tip thereof to proximate where a first knuckle of a user's thumb or finger will be located when the glove is worn; and wherein the remaining portion extends from where the first knuckle of the user's thumb or finger will be located when the glove is worn, down to the palm region;
    wherein the tip region of the index finger region has a front surface that is free of texture; and wherein the remaining portion of the index finger region from the tip region to the palm region has a texture formed therein; and
    wherein the tip regions of the thumb region, the ring finger region and the little finger region are differently textured to a texture provided on a remaining portion of each of the thumb region, the ring finger region and the little finger region.

16. The glove as defined in claim 15, wherein the texture on the tip region of the thumb region, the ring finger region and the little finger region is a diamond pattern.

17. The glove as defined in claim 16, wherein the diamond pattern is a raised pattern.

18. The glove as defined in claim 1 wherein tip region of each of the index finger region and the middle finger region is of reduced dimensions relative to the remaining portion of each of the index finger region and the middle finger region, and wherein the tip region is of a circumference that is adapted to pull the tip region tightly around the tips of the index finger and the middle finger when the glove is worn; and wherein the remaining portions are of a circumference that is adapted to cause the remaining portions to contact a rest of the index finger and the middle finger but not be pulled tightly therearound.

19. The glove as defined in claim 1 wherein tip region of each of the ring finger region and the little finger region is of reduced dimensions relative to a tip region and the remaining portion of each of the ring finger region and the little finger region; and wherein the tip region is of a circumference that is adapted to pull the tip region tightly around the tips of the ring finger and the little finger when the glove is worn; and wherein the remaining portions are of a circumference that is adapted to cause the remaining portions to contact a rest of the ring finger and the little finger but not be pulled tightly therearound.

20. The glove as defined in claim 1, wherein the wrist region, palm region, thumb region, index finger region, middle finger region, ring finger region and little finger region are comprised of a first layer of nitrile rubber that is free of or essentially free of elements, components or compounds that cause hypersensitivity or allergic reaction in persons who wear the glove.

21. The glove as defined in claim 1, wherein the tip region of the middle finger is free of texture and the remaining portion of the middle finger from the tip region to the palm region is textured; and
    wherein each of the ring finger region and the little finger region from a tip thereof to the palm region is textured.

22. The glove as defined in claim 21, wherein the layer of material in the thumb region from a tip thereof to the palm region has a texture formed therein.

23. The glove as defined in claim 1, wherein a front surface of the tip region of the middle finger is free of texture and a front surface of the remaining portion of the middle finger from the tip region to the palm region is textured;
    wherein a front surface of each of the thumb region, the ring finger region, and the little finger region from a tip thereof down to the palm region is textured; and
    wherein a front surface of the palm region and the wrist region is textured.

\* \* \* \* \*